United States Patent [19]
Pallos et al.

[11] Patent Number: 5,776,479
[45] Date of Patent: Jul. 7, 1998

[54] STABLE, GERMICIDAL FILM-FORMING TEAT-DIP SOLUTIONS

[75] Inventors: Ferenc M. Pallos, Walnut Creek, Calif.; Thomas C. Hemling, Lake Winnebago, Mo.; Dominic W. S. Wong, El Cerrito; Attila E. Pavlath, Walnut Creek, both of Calif.

[73] Assignees: The United States of America as represented by the Secretary of Agriculture, Washington, D.C.; West Agro, Inc., Kansas City, Mo.

[21] Appl. No.: 770,965

[22] Filed: Dec. 20, 1996

[51] Int. Cl.⁶ ..................................... A01N 25/32
[52] U.S. Cl. .................... 424/406; 424/405; 424/407; 424/438; 424/78.07; 424/78.3; 424/667; 424/669
[58] Field of Search ................ 424/406, 78.07, 424/78.3, 438, 405, 407, 669, 667

[56] References Cited

U.S. PATENT DOCUMENTS

| | | | |
|---|---|---|---|
| 2,863,798 | 12/1958 | Shelanski et al. | 167/17 |
| 3,028,299 | 4/1962 | Winicov et al. | 167/17 |
| 3,285,816 | 11/1966 | Kaplan et al. | 167/70 |
| 3,728,449 | 4/1973 | Cantor et al. | 424/150 |
| 3,993,777 | 11/1976 | Caughman et al. | 424/329 |
| 4,113,854 | 9/1978 | Andrews et al. | 424/78.05 |
| 4,199,564 | 4/1980 | Silver et al. | 424/80 |
| 4,271,149 | 6/1981 | Winicov et al. | 424/150 |
| 4,376,787 | 3/1983 | Lentsch et al. | 424/315 |
| 4,434,181 | 2/1984 | Marks et al. | 424/326 |
| 4,891,216 | 1/1990 | Kross et al. | 424/78 |
| 4,945,110 | 7/1990 | Brokken et al. | 514/517 |
| 5,017,369 | 5/1991 | Marhevka | 424/78 |
| 5,063,249 | 11/1991 | Andrews | 514/673 |
| 5,221,961 | 6/1993 | Adkinson | 424/616 |
| 5,368,868 | 11/1994 | Winicov | 424/667 |
| 5,529,770 | 6/1996 | McKinzie et al. | 424/78.24 |
| 5,641,498 | 6/1997 | Loosemore | 425/405 |

OTHER PUBLICATIONS

Eberhart 'Vet Clin North Am Jul. 1984 6(2) pp. 287–300 Coliform Mastitis.

*Primary Examiner*—Neil S. Levy
*Attorney, Agent, or Firm*—M. Howard Silverstein; John D. Fado; Margaret A. Connor

[57] ABSTRACT

Improved, stable, germicidal, aqueous teat-dip compositions are disclosed, which include a film-forming agent selected from the group consisting of hydroxyethylcellulose, methyl hydroxypropylcellulose, and ethylhydroxyethylcellulose, a germicidal agent, preferably iodine complexed with a non-ionic surfactant, and water to provide a solution having a viscosity of about 50 to 1000 cp. The liquid, aqueous compositions, when applied to the teats of agricultural animals, dry to form a continuous barrier film, which functions both as an effective anti-microbial agent and as an effective barrier at the mouth of the milk channel to prevent or reduce the incidence of mastitis.

12 Claims, No Drawings

STABLE, GERMICIDAL FILM-FORMING TEAT-DIP SOLUTIONS

BACKGROUND OF THE INVENTION

1. Field of the Invention

The present invention relates to and has among its objects the provision of novel germicidal compositions for protection of cow's udder from infection. In particular, the invention relates to improved germicidal film-forming compositions which are stable over a broad temperature range on storage, have germicidal activity, and when applied, dry to form a film having high adhesion and barrier properties. The compositions are useful as teat dips to provide both a continuous barrier film on the cow's teat which persists between milkings and anti-microbial activity, to thereby prevent or reduce the incidence of mastitis.

2. Description of the Art

Mastitis, a microbial infection of the milk channel in cows, is the most costly disease in U.S. animal agriculture. It is difficult to control because microbes are prevalent during and after milking, and the milk channel remains open for up to 90 minutes after milking. Preventive measures against mastitis have traditionally fallen along two lines—using a germicide solution which reduces the number of microbes, or forming a film-forming barrier over the cow's udder which prevents microbes from entering the milk channel. Some teat-dip products have incorporated both functions by including a germicide into a film-forming ingredient. For example, U.S. Pat. No. 5,063,249 issued to Andrews describes a stable, homogeneous teat dip comprising 3-(n-dodecylamino)propylamine or 2-|2-(n-dodecylamino)ethylamino|ethylamine as the germicidal ingredient and a film-forming ingredient. Only polyvinylpyrrolidone (PVP) provided a stable, homogeneous solution with 2-[2-dodecylamino)ethylamino|ethylamine. Other film-forming ingredients were tested in combination with this compound, including xanthan gum, carboxymethylcellulose, polyvinyl alcohol, hydroxyethyl cellulose, however, these did not form stable, homogeneous solutions with 2-[2-dodecylamino)-ethylamino|ethylamine.

U.S. Pat. No. 4,113,854 to Andrews at al., describes a composition for prophylactic treatment of mastitis, which comprises a film-forming polymer latex and a water soluble polymer thickening agent in an aqueous medium, the composition having a thixotropic value of 15 to 1200 dynes/cm$^2$ and a practical upper viscosity limit of 10 poise at a shear rate of 250 sec$^{-1}$.

U.S. Pat. No. 5,529,770 to McKinzie et al. describes highly viscous film-forming protective germicidal formulations which include PVP as the film-forming agent, and further include a germicidal agent, preferably complexed iodine, together with an organic thickener selected from the group consisting of alkyl celluloses, alkoxy celluloses, xanthan gum, guar gum, polyorgano sulfonic acid and mixtures thereof.

U.S. Pat. No. 5,017,369 to Marhevka describes a film-forming teat sealer composition comprised of partially hydrolyzed polyvinyl alcohol, an antimicrobial agent, such as a biguanide salt, an (alkyl)alkylenaminoglycine, a quaternary ammonium salt, and an opacifying agent, the composition being useful to form a plug-like deposit on the animal's teats.

U.S. Pat. No. 4,434,181 to Marks et al. describes a liquid teat dip composition comprising a water soluble film former such as hydroxypropyl cellulose, ethyl cellulose and methylcellulose, the bactericide chlorhexidine, and a volatile alcohol such as isopropyl alcohol in an amount not less than 80% by weight of the composition. The volatile alcohol evaporates to form a protective film.

U.S. Pat. No. 4,891,216 to Kross et al. describes a composition for forming a protective barrier while disinfecting tissues, the composition comprising two gels which when combined generate chlorine dioxide as the germicidal agent and contain a poly(sulfonic acid) salt as the film forming agent.

U.S. Pat. No. 4,199,564 to Silver et al. describes an antimicrobial animal teat dip tincture composition consisting essentially of a water soluble microbicidal lower alkanol of 1 to 3 carbon atoms, a lower alkanol-soluble film-forming polymer such as vinyl polymers, natural gum polymers or gelatin, and a water-/alkanol soluble emollient, the composition having the property of not causing irritation to the cow's teats with repeated use.

U.S. Pat. No. 4,376,787 to Lentsch describes a method for killing mastitis-causing gram negative organisms by treating an animal's teats with a thickened aqueous medium comprising an anionic surfactant, exemplified by linear alkylbenzene sulfonates, wherein the composition has a pH in the range of 2 to 5.

U.S. Pat. No. 5,221,961 to Adkinson describes a pre-milking gel composition for cleaning and sanitizing the teats and udder of agricultural animals which includes a germicide and an aqueous gelling agent to form a jelly-like mass or gel. The gelling agents include cellulose ethers or cellulose derivatives or water soluble plant and tree extrudates, seed extracts, fruit and vegetable extracts, capable of providing a jelly-like mass, without forming a separate liquid phase.

Problems with these products highlight the difficulties in protecting a cow's udder from mastitis. These include film cracking during drying, germicides which wash off when in contact with mud or water, germicides which lose their potency in the film, skin irritation due to inclusion of harsh (often polar) germicides or compounds (requiring a low pH for proper blending), inclusion of other irritating ingredients, and poor shelf-life stability.

SUMMARY OF THE INVENTION

The present invention comprises an improved formulation of a stable, germicidal, water-soluble film-forming teat-dip solution which can function both as an effective anti-microbial agent and as an effective barrier at the mouth of the milk channel to prevent or reduce the incidence of mastitis in agricultural animals.

The compositions of the invention include a film-forming agent selected from the group consisting of hydroxyethylcellulose, methyl hydroxypropylcellulose, and ethylhydroxyethylcellulose, a germicidal agent, preferably completed iodine, and water to provide a solution having a viscosity of about 50 to 1000 cp. Buffering agents are included in the solutions as necessary to provide a pH in the range of 3 to 9 (pH 4 to 7 for completed iodine). Optional ingredients may be included such as skin conditioning agents or skin moisturizing agents (emollients), wetting agents, dyes, and thickeners.

The liquid, aqueous compositions, when applied to the teats of agricultural animals, dry to form a continuous barrier film on the animal's udder and over the teat of the animal which has high adhesion characteristics and which will not substantially crack, fall off, rub off, or wash off in the field. Yet, the film can be readily removed before milking by minimal scrubbing with water or other typical pre-milking udder preparation. The compositions of the invention have the further properties of storage stability under environmental extremes and of biocide stability.

Surprisingly, the stable germicidal film-forming solutions are obtained in the absence of ingredients such as the film-forming agent PVP and in the absence of a volatile alcohol, or lower alkanol of 1 to 3 carbon atoms, which the prior art taught as needed for formulation of film-forming teat dip compositions.

The compositions of the invention find particular use as post-milking teat sanitizing solutions to provide a residual barrier film on the teat surface between milkings. The aqueous compositions are applied in an effective amount, that is, an amount, which upon drying, is sufficient to form a protective barrier film over the teat of the animal and to have anti-microbial activity against microorganisms that cause mastitis. Application is carried out by standard procedures as known in the art such as by dipping the animal's teats in the solution and allowing the solution to dry.

It has been found that the application of the compositions of the invention to an agricultural animal's teats is effective for prevention of mastitis.

In accordance with this discovery, it is an object of the invention to provide teat-dip compositions that have the dual function of reducing the number of microbes on an agricultural animal's udder and forming a film barrier over the animal's udder, to thereby prevent or reduce the incidence of mastitis.

It is also an object of the invention to provide aqueous teat-dip formulations that have physical stability over a wide temperature range that can occur during storage and have stability of the germicidal agent.

A further object of the invention is to provide compositions, which when applied to the teats of agricultural animals, form a continuous barrier film which has high adhesion characteristics, yet can be readily removed before milking using typical pre-milking udder preparation procedures.

Other objects and advantages of this invention will become readily apparent from the ensuing description.

DETAILED DESCRIPTION OF THE INVENTION

The aqueous compositions of the invention include a film-forming agent to provide a continuous barrier film on the animal's teat after drying. The film-forming agents of the invention provide a film that persists between milkings, yet can be readily removed before milking by typical pre-milking udder preparation such as washing with water or an aqueous sanitizer or by dipping the teat in a predip solution and wiping with a cloth or paper towel.

Film-forming agents useful in the present invention are selected from the group consisting of hydroxyethylcellulose, methyl hydroxypropylcellulose, and ethylhydroxyethylcellulose. Exemplary of the film-forming agents of the invention are the following non-toxic, food grade, commercially available, film-forming agents: Natrosol® (nonionic water-soluble hydroxyethylcellulose from Aqualon, Wilmington, Del.); Methocel® (methyl hydroxypropylcellulose made from cellulose and propylene oxide and available from Dow Chemical); Bermocoll E® (non-ionic, water soluble ethyl hydroxyethylcellulose from Akzo Nobel. The preferred film forming agents are Methocel® E50 LV, Methocel® K100, Methocel® F50, Natrosol® 250KR, Bermocoll E®351 FQ, Bermocoll E®411 FQ, and Bermocoll E®320 FQ.

The film-forming agent is compatible with other composition ingredients and may provide viscosity to the formulation. The film-forming agent as supplied by the manufacturer is used at a concentration of about 0.25 to 10% and preferably about 0.25 to 6.0% by weight of the composition.

The compositions of the invention also include a germicidal agent which is effective for the prevention of bovine mastitis. Germicides are selected from those that are compatible with the film-forming agents and upon combination with the film-forming agents in the aqueous compositions provide stable, homogeneous solutions. Germicides include iodine, chlorhexidene, polyhexamethylene biguanide or fatty acids. The preferred germicidal agent used in the aqueous compositions of the invention is iodine complexed with a nonionic surfactant, denoted herein as "completed iodine," with an average available (titratable) iodine level in the range of about 0.05 to 1.25%, and preferably about 0.1 to 0.75% by weight. In some instances, a given formulation such as a teat dip may have a nominal available iodine of 1%, but in fact the formulation may contain as much as 1.2% or even 1.25% by weight of available iodine. This occurs because most compositions will contain an "overage" of available iodine when manufactured, so as to allow for iodine loss over the life of the iodine product. As such, it will be understood that reference herein to average available iodine on a nominal basis covers such excess amounts. Iodine may be provided by a hydrogen or alkali metal iodide-iodine mixture, wherein the weight ratio of iodine to iodide is about 1:0.1 to 1:0.8 and preferably about 1:0.15 to 1:0.6.

Iodine may be complexed with nonionic surfactants previously described in U.S. Pat. Nos. 2,863,789; 3,028,299; 3,285,816; 3,728,449, and 5,368,868 and include ethylene oxide-propylene oxide copolymers, nonylphenol ethoxylates, alcohol ethoxylates, ethoxylated fatty acids, ethoxylated glucosides, ethoxylated sorbitol esters, alcohol alkoxylates or combinations of the various nonionic surfactants. The preferred nonionic surfactants are the ethylene oxide-propylene oxide copolymers (poloxamers) and the nonylphenolethoxylates. Poloxamer surfactants include those described in U.S. Pat. No. 5,368,868 as well as other commercially available poloxamers. Useful poloxamers include Pluronic® surfactants (BASF Corporation). The iodine-complexing agents are included in the compositions of the invention in a weight ratio of complexing agent to iodine of about 2:1 to 20:1, and preferably about 2:1 to 12:1.

The aqueous component (water) is provided in the compositions of the invention to achieve the desired ratio of other ingredients and/or achieve the desired viscosity.

Buffering agents are included in the compositions as necessary to provide a pH in the range of 3 to 9 (pH 4 to 7 for complexed iodine), to thereby maximize the stability of the composition and to minimize potential irritation to the animal's teat. Buffers suitable for the aqueous compositions of the invention are those as known in the art, for example, citrate, phosphate, lactate, acetate, and carbonate buffers.

Other ingredients may be included such as skin conditioning agents or skin moisturizing agents (emollients) such as glycerin, propylene glycol, sorbitol, polyethylene glycol, aloe vera, and lanolin or lanolin derivatives. These agents are useful to maintain a healthy teat skin and to counteract any potential irritation effect from formulation ingredients or from the environment.

Other optional ingredients include wetting agents, for example, sodium dioctylsulfosuccinate, e.g., Aerosol® TO-75 (American Cyanamid Co./Industrial Chemical Division), viscosity modifiers (thickeners), for example, xanthan gum, such as Keltrol® (Kelco, Div. of Monsanto Company), and dyes.

To improve iodine stability, iodine containing compositions may also incorporate iodate as disclosed in U.S. Pat. No. 4,271,149, which is incorporated herein by reference. Iodate, if optionally included, is typically used at a concentration of about 0.005 to 0.5%, and preferably about 0.01 to 0.4%.

The aqueous compositions of the invention are formulated to achieve final viscosities of about 50 to 1000 cP, and preferably 100 to 800 cP (Brookfield viscosity measured using Spindle #2 at 60 rpm). It is critical that the compositions remain as solutions and do not form gels.

The following table shows the weight ranges of ingredients useful for the compositions of the invention.

| INGREDIENT | BROAD RANGE | PREFERRED RANGE |
| --- | --- | --- |
| Film-forming Agent | 0.25–10% | 0.25–6% |
| Germicidal Agent (Iodine) | 0.05–1.25% | 0.1–0.75% |
| Complexing Agent:Iodine | 2:1–20:1 | 2:1–12:1 |
| Iodine:Iodide | 1:0.1–1:0.8 | 1:0.15–1:0.6 |
| Iodate (optional) | 0.005–0.5 | 0.01–0.4 |
| Emollient (optional) | 0–12% | 2–12% |
| Dye (optional) | 0–0.2% | 0.05–0.1% |
| Wetting Agent (optional) | 0–2.0% | 0.01–0.5% |
| Thickener (optional) | 0–0.5 | 0.01–0.3% |
| Buffer | To provide pH 4–7 | To provide pH 4.5–6.5 |
| Water | q.s. 100% | q.s. 100% |
| Viscosity (measured using Spindle #2 at 60 rpm) | 50–1000 cP | 100–800 cP |

A representative formulation is:

| INGREDIENT | PERCENT (W/W) |
| --- | --- |
| Water | 88.755 |
| Natrolsol ® 250KR | 0.625 |
| Pluronic ® P105 | 3.0 |
| Caustic Soda - 50% | 0.14 |
| Citric Acid, Anhydrous | 0.3 |
| Glycerin, 100% | 6.0 |
| Keltrol ® | 0.2 |
| Sodium Dioctylsulfosuccinate - 75% | 0.1 |
| Sodium Iodate | 0.02 |
| Hydriodic Acid | 0.18 |
| Iodine | 0.5 |
| Propylene Glycol | 0.18 |

The pH of the above formulation is about pH 5, and the viscosity was 325 cP measured using spindle #2 at 60 rpm.

The compositions can be prepared using commercially available starting materials. They can be conveniently prepared as follows:

1. Add Keltrol® to warm water (ca. 110°–125° F.), and mix until completely dispersed.
2. Add Pluronic® P105 surfactant BASF Corporation), sodium iodate, and glycerin, and mix until homogeneous.
3. Add 10% of the required caustic soda.
4. Add Natrosol® 250KR (nonionic water-soluble hydroxyethylcellulose from Aqualon, Wilmington, Del.), and mix until homogeneous.
5. Add Aerosol® TO-75 (sodium dioctylsulfosuccinate), citric acid, and sodium iodide-iodine (57% iodine, 20.5% Hydriodic acid), and mix until iodine is complexed with the complexing agent (Pluronic® surfactant).
6. Add the remaining caustic soda to adjust pH to 5.0.

The compositions of the invention have unique properties which make them superior teat-dips. These include shelf stability, iodine stability, lack of gel formation, and ability to form high adhesion continuous films when applied to cow's teats. Commercial products would be required to be physically stable at ambient temperatures (RT), at elevated temperatures (40° C.), and at low temperatures (–0.5° C.). Any products that showed gelling or separation are unacceptable. We discovered that the film-forming agents which provided these superior properties were hydroxyethylcellulose, methyl hydroxypropylcellulose, and ethylhydroxyethylcellulose. Certain film-forming agents such as chitosans, pectins, carboxymethyl celluloses, propylene glycol alginates (Kelcoloid® or Manucol® Ester (Kelco, Div. of Monsanto Company)), and sodium alginates (Kelgin®) did not form stable compositions having these critical properties. For example, the compositions of the invention were tested for physical stability for at least one month at room temperature (ca. 22° C.), 40° C., and in the refrigerator (ca. –0.5°–2° C.) and remained stable. In contrast, compositions prepared using film-formers taught as equivalent in the prior art, e.g., Manucol® Ester M (Kelco, Div. of Monsanto Company) and Pectin LM32 formed gels during the physical stability tests, and were not considered suitable film-forming agents for the compositions of the invention. The pectin Pectin HM Slow was not suitable as it formed an oily residue during storage.

Tests for iodine stability were carried out for 1 day at @50° C., 8 days at @50° C., 14 days at @50° C., and 2 months at room temperature. Compositions prepared from film-formers of this invention showed germicidal stability, that is, effective anti-microbial activity against microorganisms that cause mastitis. It was found that the film-forming compositions of the invention provided a continuous barrier film on cow's teats, as well as increased the rate of retention of the iodine under adverse conditions, i.e., exposure to water, mud, dirt, and other adverse environmental conditions.

A further unique feature is that the compositions can be prepared in the absence of PVP, taught as a necessary film-forming in the prior art, and also in the absence of a volatile alcohol or 1–3 carbon alkanol as taught by the prior art. Thus, the compositions of the invention represent an advance in the state of the art of teat-dips.

The compositions are particularly useful to provide post-milking teat sanitizing solutions that leave a residual barrier film on the teat surface between milkings. Typically, the compositions of the invention are applied to the teats, preferably after each milking, by dipping the teat into the liquid composition. The compositions dry to a provide a continuous protective film. While the compositions of the invention are typically "teat dips," however, as known in the art, other methods of topical applications besides teat-dipping that provide barrier films can be used. The films prepared using the teat-dip compositions of the invention have the ability to persist between milkings, but can be readily removed by typical pre-milking udder preparation such as washing with water or an aqueous sanitizer, or by dipping the teat in a predip and wiping with a cloth or paper towel.

EXAMPLE

The following example is intended only to further illustrate the invention and is not intended to limit the scope of the invention which is defined by the claims.

A series of teat dip formulations shown in the Table, below, were prepared as described above, and the physical stability was measured. In each case, the formulation showed physical stability.

| SAMPLE | % IODINE | COMPLEXOR* | FILM FORMER | % GLYCERIN | % PROP GLYCOL | % PEG-400 | % IODIDE |
|---|---|---|---|---|---|---|---|
| 14C | 0.25 | 1.38% PLURONIC | 3.33% METHOCEL E50 | | 10 | | 0.1 |
| 19C | 0.25 | 1.38% PLURONIC | 3.33% METHOCEL E50 | | | 10 | 0.1 |
| 21C | 0.25 | 1.38% PLURONIC | 2.8% METHOCEL K100 | | | 10 | 0.1 |
| 22C | 0.25 | 1.38% PLURONIC | 3.33% METHOCEL F50 | | | 10 | 0.1 |
| 24C | 0.25 | 1.38% PLURONIC | 3.33% METHOCEL E50 | 5 | | 5 | 0.1 |
| 25C | 0.25 | 1.38% PLURONIC | 3.33% METHOCEL E50 | 5 | 5 | | 0.1 |
| 28C | 0.25 | 0.625% PLURONIC P105 | 3.33% METHOCEL E50 | 5 | | 5 | 0.1 |
| 31C | 0.25 | 1.38% PLURONIC | 2.8% METHOCEL K100 | 5 | 5 | | 0.1 |
| 33B | 0.5 | 2.75% PLURONIC | 2.5% NATROSOL 99 250 GR | 6 | 5 | | 0.2 |
| 33C | 0.25 | 1.38% PLURONIC | 2.5% NATROSOL 99 250 GR | 5 | 5 | | 0.1 |
| 34C | 0.25 | 1.38% PLURONIC | 3.33% METHOCEL E50 | 5 | 5 | | 0.1 |
| 35C | 0.25 | 1.38% PLURONIC | 3.33% METHOCEL E50 | 10 | | | 0.1 |
| 39C | 0.25 | 1.38% PLURONIC | 1.0% METHOCEL E4M | 5 | 5 | | 0.1 |
| 41C | 0.25 | 0.625% PLURONIC ACT | 3.33% METHOCEL E50 | 5 | 5 | | 0.1 |
| 54C | 0.25 | 1.38% PLURONIC | 1.66% NATROSOL 99 250 KR | 5 | 5 | | 0.1 |
| 77C | 0.25 | 1.38% PLURONIC | 3.33% METHOCEL E50 | | | | 0.1 |
| 89C | 0.25 | 1.38% PLURONIC | 1.5% NATROSOL 99 250 KR | | | | 0.1 |
| 95C | 0.25 | 0.625% PLURONIC P105 | 0.75% BERMOCOLL E351 FQ | 10 | | | 0.1 |
| 105C | 0.25 | 0.625% PLURONIC P105 | 1.25% BERMOCOLL E320 FQ | 10 | | | 0.1 |
| 107C | 0.25 | 0.625% PLURONIC P105 | 1.25% BERMOCOLL E320 FQ | 10 | | | 0.1 |
| 109C | 0.25 | 0.625% PLURONIC P105 | 1.0% BERMOCOLL E351 FQ | 10 | | | 0.1 |

*COMPLEXOR LABELED 1.38% PLURONIC CONTAINS A BLEND OF 1.1% PLURONIC P-85 AND 0.28% PLURONIC P123

It is understood that the foregoing detailed description is given merely by way of illustration and that modification and variations may be made within without departing from the spirit and scope of the invention.

What is claimed is:

1. A stable, germicidal film-forming composition consisting essentially of (a) a film-forming agent selected from the group consisting of hydroxyethylcellulose, methyl hydroxypropylcellulose, and ethylhydroxyethylcellulose, (b) an effective germicidal amount of a germicidal agent consisting of a nonionic surfactant-complexed iodine, and (c) water, said composition having a pH in the range of about 3 to 9 and a viscosity of about 50 to 1000 cP measured using spindle #2 at 60 rpm, and wherein said film-forming agent is about 0.25 to 10% by weight of the composition, said iodine is present at a level of about 0.05 to 1.25% average available iodine on a nominal basis and is provided by a hydrogen or alkali metal iodide-iodine mixture, said weight ration of iodine:iodide is about 1:0.1 to 1:0.8, and said weight ratio of nonionic surfactant to iodine is about 2:1 to 20:1.

2. The composition of claim 1, wherein said film-forming agent is selected from the group consisting of a nonionic water-soluble hydroxyethylcellulose further identified as Natrosol®, a methyl hydroxypropylcellulose further identified as Methocel ®, and a non-ionic, water soluble ethyl hydroxyethylcellulose further identified as Bermocoll E®.

3. The composition of claim 1, wherein said germicidal agent is nonionic surfactant-complexed iodine and wherein said pH is in the range of about 4 to 7.

4. The composition of claim 3, wherein said nonionic surfactant-complexed iodine comprises iodine and an ethylene oxide-propylene oxide copolymer.

5. The composition of claim 4, wherein said ethylene oxide-propylene oxide copolymer is a Pluronic® surfactant.

6. The composition of claim 1, wherein the viscosity is about 100 to 800 cP.

7. The composition of claim 1, wherein said pH is controlled by a buffering agent.

8. The composition of claim 1, further including optional ingredients selected from the group consisting of wetting agents, viscosity modifiers, skin conditioning agents or skin moisturizing agents, and dyes.

9. The composition of claim 1 wherein said optional wetting agent is sodium dioctylsulfosuccinate and said optional viscosity modifier is xanthan gum.

10. The composition of claim 9 wherein said skin conditioning agents or skin moisturizing agents are selected from the group consisting of glycerin, propylene glycol, sorbitol, polyethylene glycol, aloe vera, and lanolin or lanolin derivatives.

11. The composition of claim 1, said composition being formulated as a post-milking teat dip and containing said germicidal agent in an amount effective for the prevention of mastitis.

12. A method of treating an agricultural animal's teats to provide a protective germicidal barrier film between milkings, comprising dipping said teats into the composition of claim 1 after milking, and allowing the composition to dry and form a residual film on said teats.

* * * * *